United States Patent [19]

Goh et al.

[11] Patent Number: 4,824,857

[45] Date of Patent: Apr. 25, 1989

[54] USE OF PROSTAGLANDIN $D_2$-ACTIVE SUBSTANCES

[75] Inventors: Yasumasa Goh, 91-5, Kawashimarokunotsubo-cho, Nishiko-ku, Kyoto-shi, Kyoto-fu; Osamu Hayaishi, Kyoto, both of Japan

[73] Assignees: Yasumasa Goh, Kyoto; Research Development Corporation of Japan, Tokyo, both of Japan

[21] Appl. No.: 45,965

[22] Filed: May 4, 1987

[30] Foreign Application Priority Data

May 16, 1986 [JP] Japan ................. 61-113140

[51] Int. Cl.$^4$ ............. A61K 31/415; A61K 31/215; A61K 31/19; A61K 31/557
[52] U.S. Cl. ..................... 514/398; 514/530; 514/573; 514/913
[58] Field of Search .............. 514/359, 398, 423, 573, 514/530, 913

[56] References Cited

U.S. PATENT DOCUMENTS 4,599,353 7/1986 Bito .................................... 514/530

FOREIGN PATENT DOCUMENTS 0001418 1/1984 Japan .

OTHER PUBLICATIONS

Chiryo 68, 1207–1213 (1986)–Translation of Column 1, Line 26–Column 2, Line 28.
Stern, E. A. et al., Invest., Opthalmol., Vis. Sci., 22, 588–598 (1982).
Kulkarni, P. S. et al., Invest. Opthalmol, Vis, Sci., 26, 1178–1182.
Bito, L. Z. Exp. Eye. Res., 38, 181–194, (1984).
Kulkarni, P. S., et al., Invest, Opthalmol, Vis. Sci., 23, 383–392 (1982).
Bito, L. Z., Exp. Eye Res., 39, 807–829 (1984).
Giuffre, G., Graefe's Arch. Clin. Exp. Opthalmol, 222, 139–141 (1985).
Van Alphen, G.W.H.M., et al., Doc. Opthamol, 42 397–415 (1977).
Masuda, K. et al., Japanese J. Opthamol., 17, 300–309, (1973).
Moses, R. A. et al., Ann. Opthalmol, 13, 721–723 (1981).
Camras, C. B. et al., Invest. Opthalmol., Vis. Sci., 16, 1125–1134 (1977).
Lee, Ping–yu, "Invest. Opthalmol & Vis. Sci.", 25, 1087–1093, 1984.

*Primary Examiner*—Douglas W. Robinson

[57] ABSTRACT

Method of treatment of ocular hypertension and glaucoma which comprises administering an effective amount of prostaglandin $D_2$-active substance to a subject in need of such treatment.

7 Claims, 6 Drawing Sheets

USE OF PROSTAGLANDIN D₂-ACTIVE SUBSTANCES

FIELD OF THE INVENTION

The present invention relates to a use of prostaglandin $D_2$-active substances for ameliorating ocular hypertension and treating glaucoma. More particularly, the present invention provides a medicament containing a prostaglandin $D_2$-acting substance as an active ingredient and a method of treating ocular hypertension and glaucoma.

BACKGROUND OF THE INVENTION

Glaucoma is an eye disease which is characterized by an increase of intraocular pressure. The increase of the pressure is caused by either a decreased aqueous outflow through Schlemm's canal or an abnormally increased secretion of aqueous humor. The mechanism for onset of glaucoma has not yet been sufficiently clarified. Conventional therapeutics consist of administration of pilocarpin, epinephrine, adrenergic beta-blocker, and the like. However, continuous use of adrenergic beta-blocker results in weakening in its action. In severe cases, surgical operations have been often conducted to decrease intraocular pressure. It is also known that among prostaglandin(PG)s, prostaglandins $D_3$, $E_1$, $E_2$, $E_3$, $F_{2\alpha}$ and $F_{2\alpha}$ derivatives show the activity of reducing intraocular pressure. (Chiryo 68, 1207–1213 (1986), Invest. Ophthalmol. Vis. Sci. Vol. 22, p. 588 (1982), 26, 1178–1182 (1985), Exp. Eye Res. 38, 181–194 (1984) and USP 4599353). Some of these prostaglandins, however, have a tendency to cause inflammational reactions. Furthermore, E and F type PGs incur a transient rise in intraocular pressure (IOP) before IOP reduction when administered in higher dose, which may aggravate the disease condition. Therefore, these PGs cannot be said to be appropriate for treatment of glaucoma.

In the course of the study on the pharmacological activity of prostaglandin $D_2$-active substance, the present inventors have found that the prostaglandin $D_2$-active substance can reduce the IOP without being accompanied by the transient rise in IOP.

The action of $PGD_2$ per se on IOP has been reported in two articles. In the first article (Invest. Opthalmol. Vis. Sci. 23, 383–392, 1982), it was reported that $PGD_2$ showed IOP raising activity in rabbits. In the second article (Exp. Eye Res. 38, 181–194, 1984, corresponding to U.S. Pat. No. 4,599,353) which deals mainly with $PGF_{2\alpha}$ and its derivatives, $PGD_2$ was administered to cats but the obtained result was not analyzed. In addition, according to the present inventors' analysis, the said data ($-2\pm0.8$ mmHg, n=6) was not significant by Student's t-test indicating that $PGD_2$ was not effective in that experiment. The reason why $PGD_2$, contrary to the present inventors' finding, raised IOP or was ineffective on IOP in the experiments of the previous workers is not sufficiently clear. However, one of the causes may be attributed to the fact that the experimental animals used therein were, in our assumption, normal or lower IOP animals, in view of the present invention's finding that $PGD_2$ does not reduce IOP of the normal or lower IOP rabbits. The present inventors, in contrast to the previous workers, used high IOP animals selected from the available rabbits and discovered that $PGD_2$ has a reducing activity on IOP in such animals. Advantageously, $PGD_2$ has been found by the present inventors to cause no side effect such as hyperemia and flare which were observed on administration of $PGE_2$, $PGF_{2\alpha}$ and $PGF_{2\alpha}$ derivatives. Furthermore, the present inventors also confirmed the above mentioned activity of $PGD_2$ in human subjects.

SUMMARY OF THE INVENTION

In one aspect, the present invention provides a method of treatment of ocular hypertension and glaucoma which comprises administering an effective amount of prostaglandin $D_2$-active substance to a subject in need of such treatment.

In another aspect, the present invention provides a use of prostaglandin $D_2$-active substance for the manufacture of a medicament for treatment of ocular hypertension and glaucoma.

In a further aspect, the present invention provides a pharmaceutical composition for treating ocular hypertension and glaucoma comprising an effective amount of prostaglandin $D_2$-active substance in association with a pharmaceutically acceptable carrier, diluent or excipient.

DETAILED DESCRIPTION AND PREFERRED EMBODIMENTS

Figure 1:
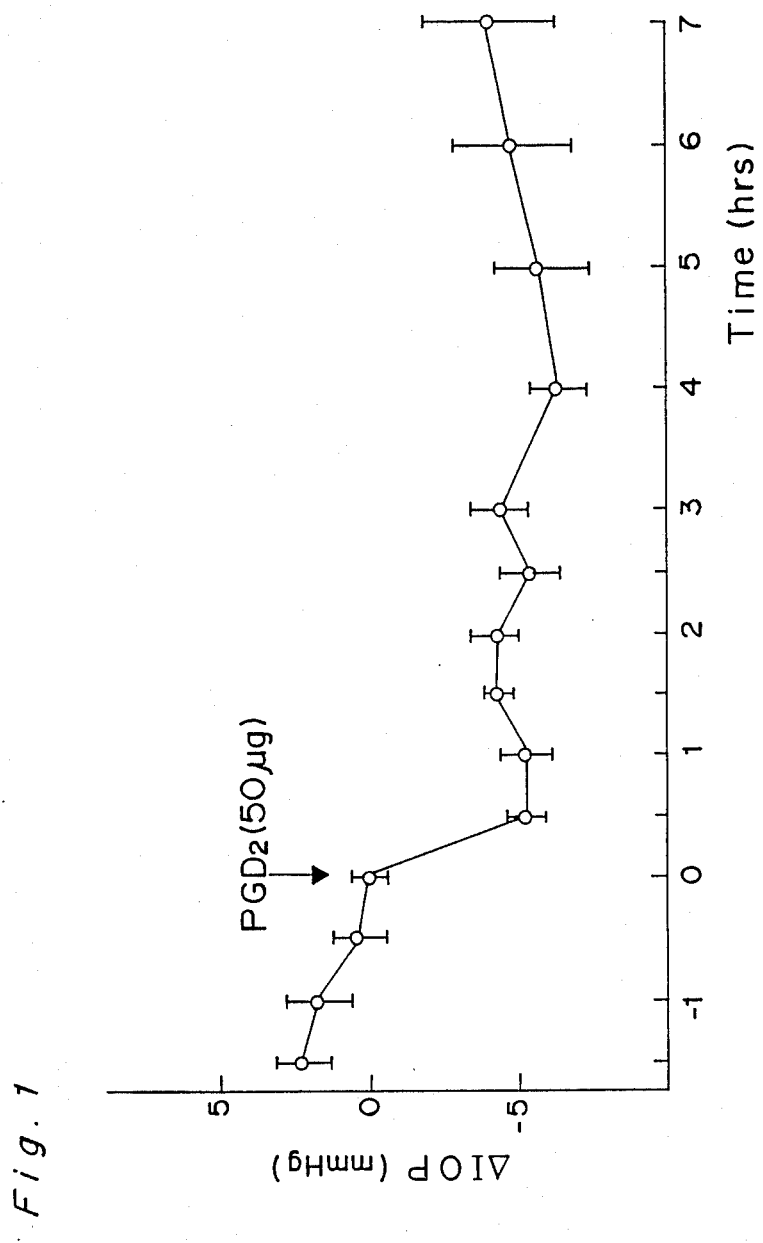

The term "treatment" herein is intended to cover all controls of the disease including prevention, sustention and therapy.

The prostaglandin $D_2$-active substance to be used in the present invention includes prostaglandin $D_2$ and its derivatives. They include the compounds of the formula:

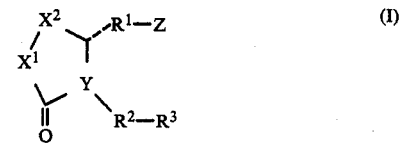

(I)

wherein $X^1$-$X^2$ is —$CH_2$—$CH(OH)$— or —NH—CO—, Y is >CH— or >N—, Z is carboxy group or its functional derivative, $R^1$ is saturated or unsaturated, bivalent lower aliphatic hydrocarbon residue, $R^2$ is saturated or monoolefinically unsaturated bivalent lower aliphatic hydrocarbon residue having an OH group on the carbon atom at the third position from Y, provided that $R^1$ and $R^2$ are simultaneously saturated or unsaturated, and $R^3$ is a monovalent saturated lower aliphatic hydrocarbon residue, and pharmaceutically acceptable salts thereof.

In the above formula, wherein $X^1$-$X^2$ is —NH—CO—, the 5-membered ring including $X^1$-$X^2$ is in tautomerism represented by the following equilibrium:

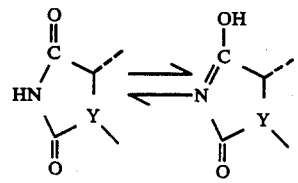

It is to be understood that both of the said groups are substantially the same and tautomeric forms of the compounds having such groups are included in the prostaglandin $D_2$-active substance to be used in the present invention.

The functional derivatives of the carboxy group represented by Z includes esters and amides conventionally used as a protective group for carboxy group. Examples of the esters are aliphatic esters such as lower alkyl esters (e.g., methyl ester, ethyl ester, propyl ester, isopropyl ester, butyl ester, isobutyl ester, tertiary butyl ester, pentyl ester, 1-cyclopropyl ethyl ester, etc.), lower alkenyl esters (e.g., vinyl ester, allyl ester, etc.), lower alkynyl esters (e.g., ethynyl ester, propinyl ester, etc.), lower alkoxy-lower alkyl esters (e.g., methoxymethyl ester, 1-methkoxyethyl ester, etc.), and aromatic esters such as optionally substituted aryl esters (e.g., phenyl ester, tolyl ester, tertiary butylphenyl ester, salicyl ester, 3,4-dimethoxyphenyl ester, etc.), and aryl lower alkyl esters (e.g., benzyl ester, trityl ester, benzhydryl ester, etc.).

The bivalent lower aliphatic hydrocarbon residues of $R^1$ and $R^2$ are the straight or branched chain aliphatic hydrocarbon residues having preferably not exceeding 6 carbon atoms at the straight-chain portion and not exceeding 3 carbon atoms at each side chain where side chains are present. These are in such relation that, when one is saturated, the other is also saturated, while when one is unsaturated, the other is also unsaturated. $R^2$ contains at least 3 straight chain carbon atoms, with a hydroxyl group on the carbon atom at the third position from Y and, when unsaturated, is monoolefinical. The monovalent saturated lower aliphatic hydrocarbon residue $R^3$ includes the straight or branched chain aliphatic hydrocarbon residues having preferably not exceeding 6 carbon atoms at the straight-chain portion and not exceeding 3 carbon atoms at each side chain where side chains are present, and those which are partially or wholly cyclic.

Examples of the preferred groups as $R^1$ are $-(CH_2)_6-$, $-CH_2CH=CH(CH_2)_3-$, $-(CH_2)_4CH=CH-$, $-(CH_2)CH=CH(CH_2)_4-$, etc.

Examples of the preferred groups as $R^2$ are $-(CH_2)_2CH(OH)-$, $-CH=CHCH(OH)-$, $-CH=CHC(CH_3)(OH)-$, etc.

Examples of the preferred groups as $R^3$ are $-(CH_2)_5H$, $-C(CH_3)_2(CH_2)_4H$, $-CH_2CH(CH_3)(CH_2)_4H$, cyclohexyl, etc. It is desirable for them to have the same steric configurations as in natural prostaglandin-$D_2$.

Since prostaglandin $D_2$ itself is somewhat unstable, stable compounds having similar activity are more preferable in many cases. Examples of such compounds are 1-(3-cyclohexyl-3α-hydroxypropyl)-2,4-dioxoimidazolidine-5α-heptanoic acid and 16,16-dimethyl-prostaglandin $D_2$.

In the above compounds wherein Z is a carboxyl group, the compounds having the preferred groups as exemplified above as $R^1$ and $R^2$ are known. The compounds having the groups other than these can be prepared in a similar manner to the process for preparing the above known compounds (Adv. PG. TX. LT. Res., 15, 295 and 299, 1985).

The compounds wherein Z is a functional derivative of carboxyl group include known compounds as well as novel compounds.

The novel compounds can be prepared, for example, by reacting alcohols, amines, or reactive derivatives at their hydroxyl group or amino group with the corresponding free carboxylic acid or its reactive derivative. Examples of the reactive derivative in the above carboxyl group are acid halides, acid anhydrides, activated esters, and activated amides. Among the acid halides, acid chloride is frequently used. Acid anhydrides include symmetric anhydride and mixed anhydride. The latter includes, for example, dialkyl phosphate mixed anhydride, dialkyl phosphite mixed anhydride, alkyl carbonate mixed anhydride, aliphatic carboxylic acid (e.g., pivalic acid, trichloroacetic acid) mixed anhydride, etc.

As the activated esters, methyl ester, ethyl ester, cyanomethyl ester, p-nitrophenyl ester, N-hydroxysuccinimide, etc. may be used. As the activated amides, amides with imidazole, dimethyl imidazole, and triazole may be used. The reactive derivatives of the above hydroxyl group include halides and sulfonic acid (e.g., methanesulfonic acid, toluenesulfonic acid) esters, etc.

As the reactive derivative in the above amino group, there may be used the Schiff bases with aldehydes (e.g., acetaldehyde, isopentanal, benzaldehyde), reaction products with silyl compounds (e.g., trimethylsilyl chloride, trimethylsilyl acetamide), reaction products with phosphoric compounds (e.g., phosphorus trichloride, phosphorus oxychloride), etc. When a free carboxylic acid is used, the reaction is advantageously effected in the presence of a condensing agent. Examples of the condensing agents are N,N'-dicyclohexylcarbodiimide, N-cyclohexyl-N'-morphorinoethyl carbodiimide, N,N'-diisopropyl carbodiimide, N-ethylbenzisoxasolium salt, 2-chloro-1-methyl pyridinium salt, N,N'-carboxyl diimidazole, phosphorus trichloride, phosphorus oxychloride, etc. The reaction is usually carried out in a solvent. The solvents include dioxane, methylene chloride, tetrahydrofuran, dimethylformamide, pyridine, benzene, toluene, xylene etc.

A preferred method of preparation is shown, as follows:

To a dry acetone solution (2 ml) containing prostaglandin $D_2$ (10 mg) kept at $-10°$ C. under nitrogen stream are added triethylamine (10 mg) and isobutyl chloroformate (7.6 mg), followed by addition of an acetone solution containing an excess amount of alcohol or amine, and the mixture is stirred overnight at room temperature. The solvent is distilled off, and the residue is purified for example by chromatography.

The dosage of the above prostaglandin $D_2$-active substance is usually 0.01 to 100 mg/kg, which is administered by such routes as topical, oral, intrarectal, intraocular, intravascular, etc. For administration, the active ingredient may be mixed with pharmaceutical carriers such as organic or inorganic, solid or liquid vehicles suitable for the particular administration route such as topical, oral, intrarectal, intraocular, intravascular, etc. and administered in the form of a conventional pharmaceutical preparation. Such preparation include solids such as tablets, granules, powders, capsules, and liquids such as solutions, suspensions, emulsions, etc. The above carriers include starch, lactose, glucose, sucrose, dextrin, cellulose, paraffin, fatty acid glyceride, water, alcohol, etc. If necessary, auxiliaries, stabilizers, wetting agents, emulsifiers, lubricants, binders, and other conventional additives may be added.

The prostaglandin $D_2$-active substance has an advantage that it remarkably reduces IOP without being accompanied with any transient rise in IOP in a wide range of dosages. Accordingly, the prostaglandin $D_2$-active substance is useful for treating or alleviation of glaucoma. Also, the prostaglandin $D_2$-active substance has the advantage that it exhibits the IOP reducing action in case of high IOP and not in the case of lower than normal value. Accordingly, the prostaglandin $D_2$- active substance gives no side effect even when used for prevention of glaucoma. In these respects, the prostaglandin $D_2$-active substance has excellent advantages which have not seen in conventional drugs.

The present invention is now illustrated in further detail by way of the following Examples.

Formulation Example 1

(a) Prostaglandin $D_2$: 10 mg
(b) Phosphate buffer (pH 7.3): 10 ml

The above (a) and (b) are filled into separate vials. At the time of use, they are dissolved together to make an ophthalmic solution or injection.

Formulation Example 2

(a) Prostaglandin $D_2$: 10 mg
(b) Sesame oil: 10 ul

The above (a) and (b) are filled into separate vials. At the time of use, they are dissolved together.

Formulation Example 3

Prostaglandin $D_2$: 50 mg
Lactose: 245 mg
Magnesium stearate: 5 mg

The above compounds are mixed according to conventional procedure, granulated, and filled in a gelatine hard capsules.

Prostaglandin $D_2$ in the above Formulation may be replaced by other $PGD_2$-active ingredients.

Example 1

Albino rabbits (female, 1.5–3.5 kg) were restrained in metal rabbit holders and IOP was measured with an applanation pneumatonograph (made by Alcon). Prior to measurement of IOP, Benoxil 0.4% solution (oxybuprocaine hydrochloride 0.4% solution, made by Santen Seiyaku) was instilled to effect surface anaesthetization. Subsequently, a buffer containing a test substance was administered topically to one eye and a buffer only to the other eye which served as a control.

As the test substance, prostaglandin $D_2$ (50 ug) was used, which was administered as a solution in a phosphate buffer of pH 7.3 (50 ul). The experiments were repeated 9 times, and the average value thereof was adopted.

The results in the case where rabbits showed an initial IOP of 19.2±1.32 mm Hg are showed in FIG. 1. It can be seen from FIG. 1 that the IOP showed a remarkable reduction at 30 minutes after the administration of prostaglandin $D_2$ (shown as $PGD_2$ in the drawing) which lasted to at least 7 hours later. The IOP returned approximately to the original value after 20 to 24 hours.

Figure 2:
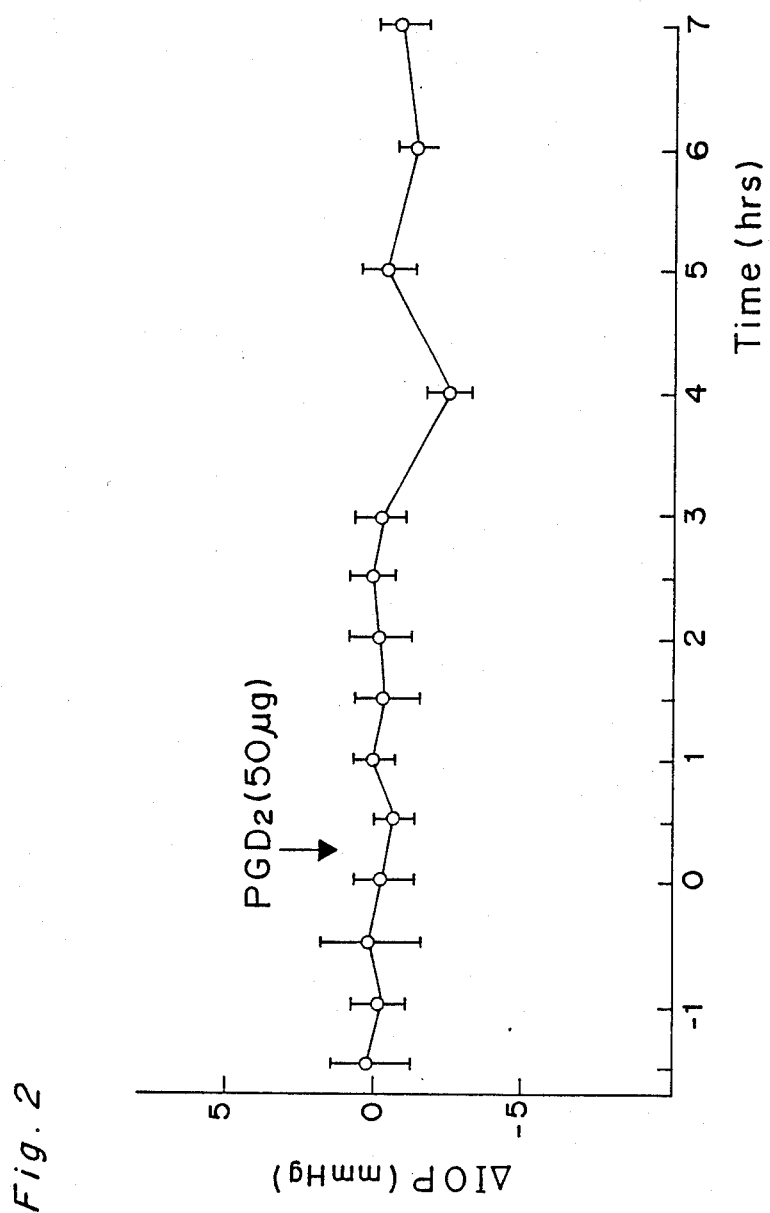

The results in the case where rabbits showed an initial IOP of 13±0.71 mm Hg are shown in FIG. 2. It can be seen from FIG. 2 that prostaglandin $D_2$ did not exhibit the effect to the rabbits having low IOP (It is to be noted that since the above IOP measuring device is one for human use, the reading of the IOP value does not necessarily agree with the absolute IOP value of a rabbit). The test results are shown by using $\Delta IOP = IOP$ exp (intraocular pressure of the eyes to which test substance was administered) $-IOP$ cont (intraocular pressure of control eyes).

Example 2

The test procedure of Example 1 was repeated except that 1-(3-cyclohexyl-3α-hydroxypropyl)-2,4-dioxoimidazolidine-5α-heptanoic acid of the following formula:

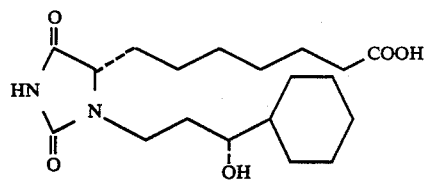

Figure 3:
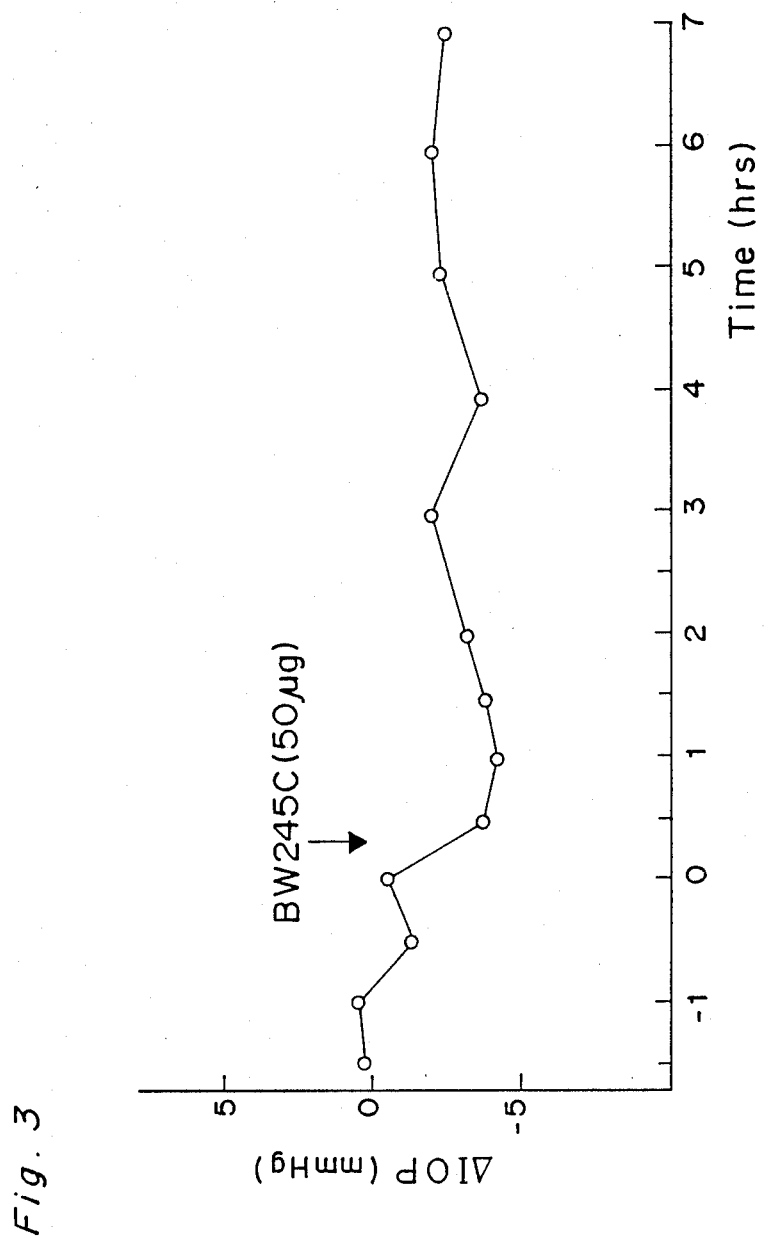

(abbrev. BW245C) was used in place of prostaglandin $D_2$. The results are shown in FIG. 3. From FIG. 3 it can be seen that, on administration of BW245C to a high IOP rabbit, remarkable IOP reduction is shown at 30 minutes after administration as in prostaglandin $D_2$.

Example 3

Figure 4:
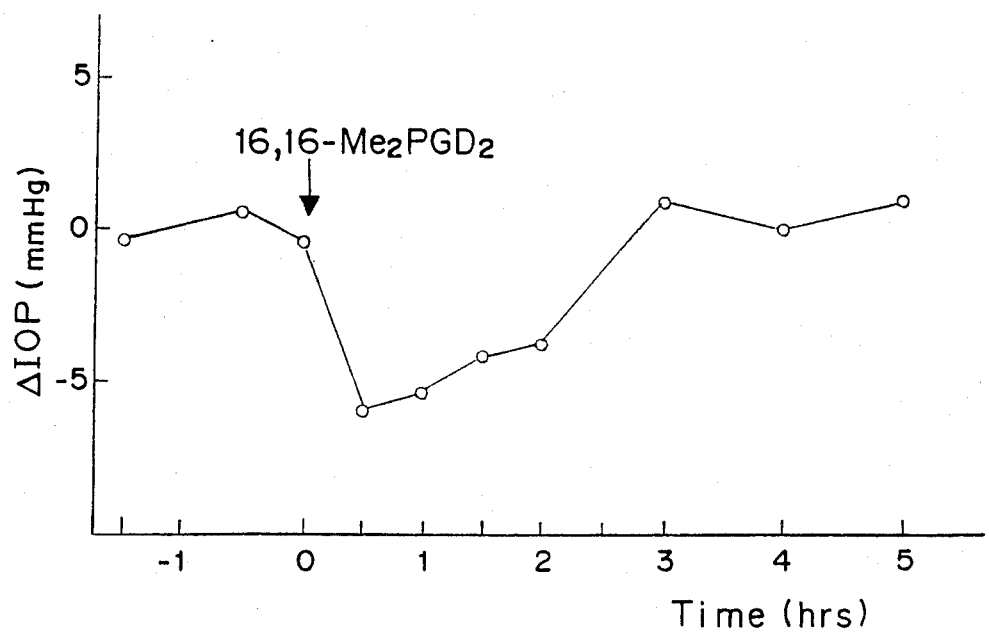

The test procedure of Example 1 was substantially repeated using 16,16-dimethylprostaglandin $D_2$ (abbrev., 16,16-Me$_2$ $PGD_2$) as a test substance in place of prostaglandin $D_2$. However, as this compound is hardly soluble in water, it was administered in the form of a solution in olive oil (for 50 ug instillation). To the control eye, the same amount of olive oil was administered. The initial IOP of the rabbits (n=3) was 29.0±3.9 mm Hg. The results are shown in FIG. 4. It can be seen from FIG. 4 that 16,16-Me$_2$ $PGD_2$ also shows remarkable IOP reduction at 30 minutes after the administration. In this case, however, the sustaining time was slightly shorter.

Example 4

Figure 5:
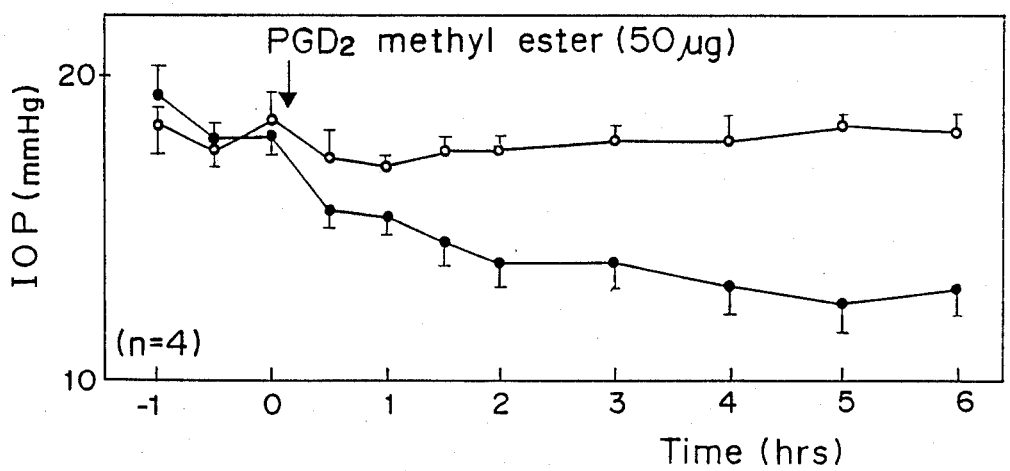

The test procedure of Example 1 was substantially repeated using prostaglandin $D_2$ methyl ester as a test substance in place of prostaglandin $D_2$. However, as this compound is hardly soluble in water, it was administered in the form of a solution in olive oil (for 50 ug instillation). To the control eye, the same amount of olive oil was administered. The initial IOP of the rabbits (n=4) was 19.3±1.1 mm Hg. The results are shown in FIG. 5. It can be seen from FIG. 5 that $PGD_2$ methyl ester also shows remarkable IOP reduction at 30 minutes after the administration.

Example 5

Figure 6:
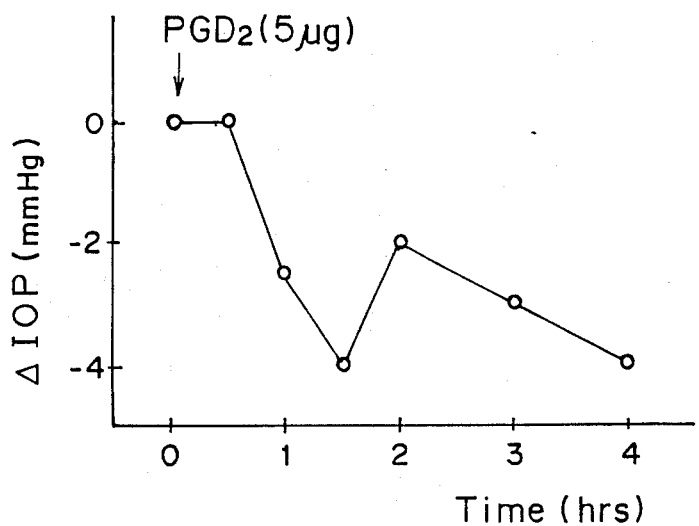

The test procedure of Example 1 was substantially repeated using a human subject in place of rabbits. The dose of $PGD_2$ was 5 μg. The initial IOP was 18.0. The results are shown in FIG. 6. It can be seen from FIG. 6 that $PGD_2$ shows remarkable IOP reduction in humans.

Example 6

Figure 7:
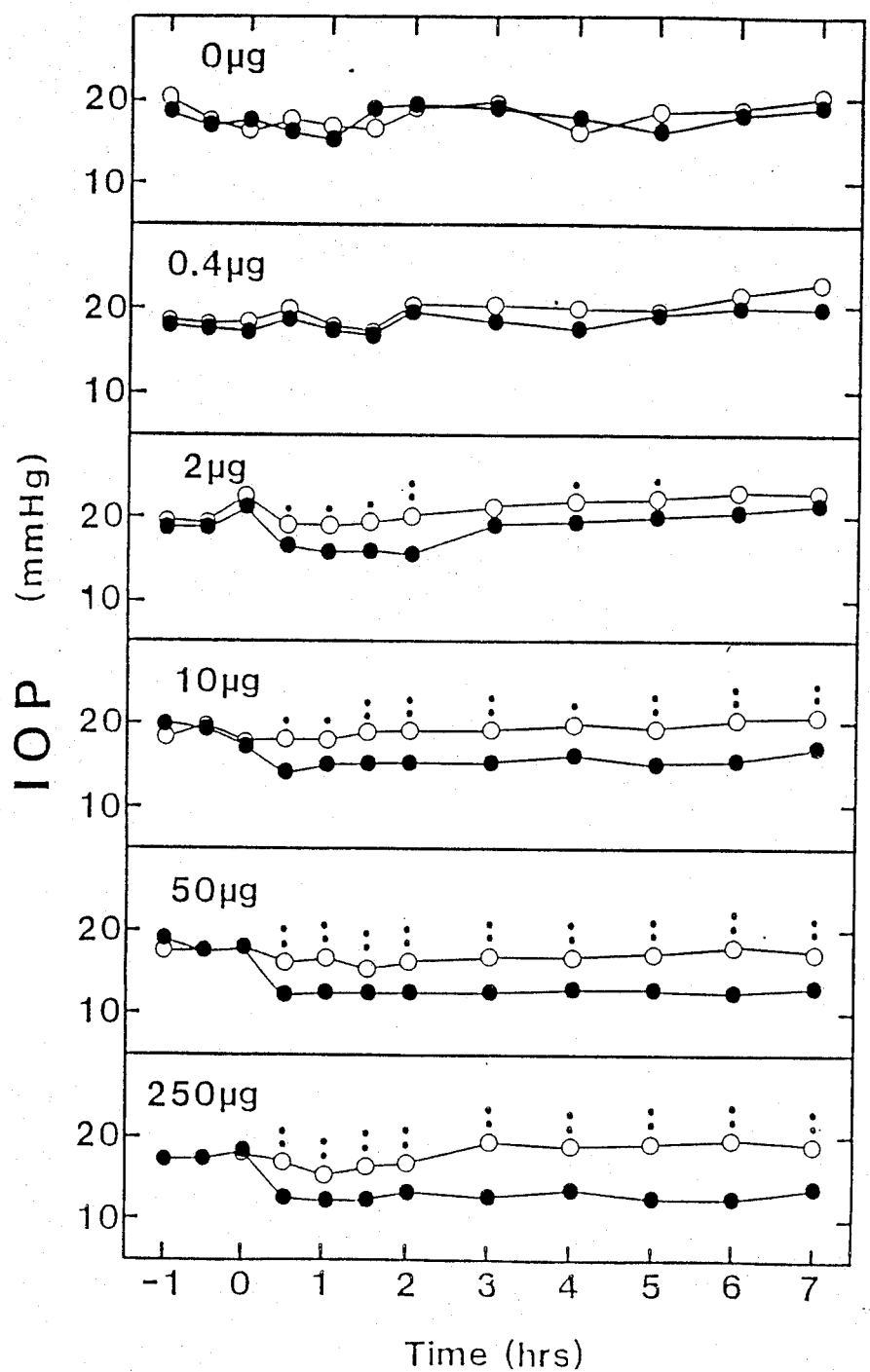

Albino rabbits weighing 2–2.5 kg were restrained in rabbit holders. $PGD_2$ was dissolved in 100 mM potassium phosphate (pH 7.3) and administered topically to one eye. The other eye received the vehicle alone. IOP values were measured for various doses as in Example 1. The results are shown in FIG. 7. From FIG. 7, it can be seen that $PGD_2$ is effective at doses of 2 μg and more.

Example 7

Using the test procedure of Example 6, various test compounds were administered at a 50 μg dose. Hyperemia and flare were monitored by slit-lamp examination. Irritatory response was defined by lid-closing. The results are shown in the following Table in which all scores are shown in four grades (−, ±, +, ++) as an average of at least 4 animals during four-hour observation.

| Compound | Irritation | Hyperemia | | Flare |
| | | conjunctiva | iris | |
| --- | --- | --- | --- | --- |
| $PGD_2$ | − | − | − | − |
| $PGE_2$ | ++ | ++ | ++ | + |
| $PGF_{2\alpha}$ | ++ | ++ | ++ | ± |

It can be seen from the above results that $PGD_2$ has no irritation, hyperemia and flare at a dose which is toxic for $PGE_2$ and $PGF_{2\alpha}$.

Example 8

Figure 8:
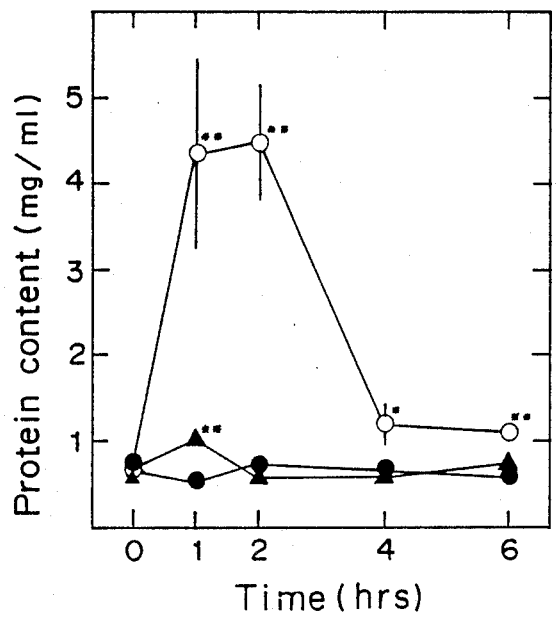

In the test procedure of Example 7, $PGD_2$ (50 μg), $PGE_2$ (2 μg) and $PGF_{2\alpha}$ (10 μg) were administered as the test compounds. Aqueous humor was carefully withdrawn from the eye by a needle under a binocular microscope and protein content was determined using bovine serum albumin as a standard. The results are shown in FIG. 8. From FIG. 8, it can be seen that protein content does not significantly change after administration of $PGD_2$ while it increases after administration of $PGE_2$ or $PGF_{2\alpha}$.

In FIGS. 7 and 8, statistical significance was determined by paired t-test and Duncan's multiple range test, respectively. * ... $P<0.05$, ** ... $P<0.01$.

What is claimed is:

1. A method of treatment of ocular hypertension and glaucoma which comprises administering from about 2 to about 50 μg, per eye, of prostaglandin $D_2$-active substance selected from the group consisting of prostaglandin $D_2$, prostaglandin $D_2$ methyl ester, 1-(3-cyclohexyl-3α-hydroxypropyl)-2,4-dioxoimidazolidine-5α-heptanoic acid, and pharmaceutically acceptable salts thereof, to a subject in need of such treatment.

2. The method according to claim 1, in which the prostaglandin $D_2$-active substance is selected from the group consisting of prostaglandin $D_2$ and pharmaceutically acceptable salts thereof.

3. The method according to claim 1, in which the said prostaglandin $D_2$-active substance is formulated into a solution for use.

4. The method according to claim 3, in which said solution is formulated using a solvent system comprising water or vegetable oil.

5. The method of claim 1, wherein the dosage ranges from about 5 μg to 50 μg, per eye.

6. The method according to claim 1, in which the prostaglandin $D_2$-active substance is 1-(3-cyclohexyl-3α-hydroxypropyl)-2,4-dioxoimidazolidine-5α-heptanoic acid or pharmaceutically acceptable salt thereof which is administered in an anti-ocular-hypertension or anti-glaucoma effective amount.

7. The method according to claim 1, in which the prostaglandin $D_2$-active substance is prostaglandin $D_2$ methyl ester which is administered in an anti-ocular-hypertension or anti-glaucoma effective amount.

* * * * *